US00RE41159E

(19) United States
(12) Reissued Patent
Bourguignon

(10) Patent Number: US RE41,159 E
(45) Date of Reissued Patent: Mar. 2, 2010

(54) MODIFYING AND SUPPLYING LIQUID NUTRITIONAL FEEDING

(75) Inventor: Michel Moreau Bourguignon, Lasson (FR)

(73) Assignee: Nestec S.A., Vevey (SE)

(21) Appl. No.: 10/194,725

(22) PCT Filed: Jan. 21, 1998

(86) PCT No.: PCT/EP98/00522

§ 371 (c)(1),
(2), (4) Date: Jul. 28, 1999

(87) PCT Pub. No.: WO98/37856

PCT Pub. Date: Sep. 3, 1998

Related U.S. Patent Documents

Reissue of:
(64) Patent No.: 6,336,912
Issued: Jan. 8, 2002
Appl. No.: 09/355,363
Filed: Jul. 28, 1999

(30) Foreign Application Priority Data

Feb. 28, 1997 (EP) ..... 97200596

(51) Int. Cl.
*A61M 31/00* (2006.01)

(52) U.S. Cl. ..... 604/65

(58) Field of Classification Search ..... 604/82–88, 604/244, 251, 252, 258, 262, 403, 405, 408, 604/411, 413–416, 246
See application file for complete search history.

(56) References Cited

U.S. PATENT DOCUMENTS

| | | | | | |
|---|---|---|---|---|---|
| 4,392,850 | A | * | 7/1983 | Elias et al. | 604/82 |
| 4,392,851 | A | * | 7/1983 | Elias | 604/82 |
| 4,601,704 | A | * | 7/1986 | Larkin | 604/87 |
| 5,385,547 | A | * | 1/1995 | Wong et al. | 604/87 |

FOREIGN PATENT DOCUMENTS

| | | |
|---|---|---|
| DE | 3920775 A1 | 1/1991 |
| EP | 0 696 448 A2 | 2/1996 |
| WO | WO 85/03432 | 8/1985 |
| WO | WO 95/16490 | 6/1995 |

* cited by examiner

*Primary Examiner*—Manuel A Mendez
(74) *Attorney, Agent, or Firm*—Gary M. Lobel

(57) ABSTRACT

The present invention relates to an apparatus for modifying and feeding a liquid nutritional feeding composition. The apparatus comprises a chamber (3) for receiving a beneficial agent for modifying a liquid nutritional feeding composition, the chamber has an inlet (7) connectable to a container (5) that contains the nutritional feeding composition and an outlet (13) connectable to a feeding means (8,9). A pumping means is associated with the chamber (3) for pumping the nutritional feeding composition from the container into the chamber and back into the container to mix the beneficial agent with the nutritional feeding composition before the outlet (13) of the chamber is connected to the feeding means (8,9). The chamber (3) may comprise at least one flexible wall capable of being squeezed and released for pumping the nutritional feeding composition. The invention also relates to a method for modifying and feeding a liquid nutritional feeding composition.

16 Claims, 3 Drawing Sheets

15
7
3
14
4
12
16
13

MODIFYING AND SUPPLYING LIQUID NUTRITIONAL FEEDING

Matter enclosed in heavy brackets [ ] appears in the original patent but forms no part of this reissue specification; matter printed in italics indicates the additions made by reissue.

TECHNICAL FIELD

The present invention relates to an apparatus and method for modifying and feeding a liquid nutritional feeding composition, in particular to its modification by adding a beneficial agent to the liquid feeding composition, before feeding said liquid feeding composition.

BACKGROUND

It is known to enterally or intravenously feed liquid nutrition to patients who are not able to eat by themselves. Such liquid meals are normally provided in hangable containers such as bottles or plastic bags and are fed from the containers through a tube to the patient. A number of different liquid nutritional feeds are available for varying the nutritional intake of the patient. Nevertheless, there is a need to tailor the liquid meals to the patient's individual needs. This is known to be done by adding beneficial agents such as for example nutrients, probiotics and medicaments to the liquid nutritional feed. The adding of such beneficial agents should, for some applications, preferably take place just before the feeding starts as a premature mixing of the liquid nutritional feed and the beneficial agent may considerably decrease the quality and shelf-life of the liquid nutritional feed.

The liquid meals provided in hangable containers such as bottles or plastic bags are generally aseptically processed or terminally retorted before use. This increases the shelf life of the liquid meal. For providing an aseptic feed to the patient, the container is connected directly via a feeding tube or line to the patient. Any opening of the system for adding a beneficial agent increases the risk for bacterial growth or contamination.

A closed-line system for the modifying and feeding of patients is therefore desirable.

The prior art discloses closed-line systems wherein a liquid nutritional feeding composition is passed through a chamber comprising a beneficial agent before entering the patient feeding line. The beneficial agent is mixed or dissolved in the liquid nutritional feeding composition when it passes through the chamber.

In order to homogenise the feed to the patient in this type of feeding system and thus prevent an over concentration of the beneficial agent, it is necessary to control the release of the beneficial agent. Consequently, a beneficial agent in controlled release form is used, i.e. an agent the solubility of which is delayed or retarded. For example, supplying of the liquid nutritional feed relates the beneficial agent over a period of 2 to 24 hours. Furthermore, although the controlled release form allows the beneficial agent to be released over a period, in-homogeneity may be experienced in the start-up phase due to the protective coating on the beneficial agents.

SUMMARY OF THE INVENTION

It is an object of the invention to provide an improved system for modifying and feeding a homogeneous mixture of a liquid nutritional feed and a beneficial agent. In particular to provide a delivery apparatus useable with a beneficial agent in a non-controlled release form.

It is a further object of the invention to provide a closed-line system for modifying and feeding a mixture of a liquid nutritional feed composition and a beneficial agent by allowing the operations to take place without opening the system to bacteria or contamination.

Accordingly, in a first aspect, the invention concerns an apparatus for modifying and feeding a liquid nutritional feeding composition comprising, a chamber for receiving a beneficial agent for modifying a liquid nutritional feeding composition, the chamber having an inlet connectable to a container containing the nutritional feeding composition and an outlet connectable to a feeding means, and a pumping means associated with the chamber for pumping the nutritional feeding composition from the container into the chamber and back to the container for mixing the beneficial agent into the nutritional feeding composition.

Thus, the present invention provides an apparatus for modifying and feeding a liquid nutritional feeding composition which allows the addition of a beneficial agent to the liquid feed immediately before the feeding commences, which addition of the beneficial agent is done without an opening and reclosing of the system. The mixing of the beneficial agent and the liquid feeding is conducted by pumping means arranged to pump liquid feed from the container into the chamber and liquid and beneficial agent back into the container. After end mixing, the chamber is connected to feeding means for feeding of the mixture to the patient.

It has been found that a homogeneous modification and feeding can be obtained with the feeding system according to the invention. Furthermore, it has been found that the mixture of liquid feed and the beneficial agent is stable during 48 hours' feeding.

In a particularly advantageous embodiment of the invention the pumping means is adapted to vary the volume of the chamber being used for pumping of the nutritional feeding composition. Especially preferred is an embodiment of the invention wherein the chamber comprises at least one flexible wall capable of being squeezed and released for pumping of the nutritional feeding composition. For example, a wall of plastic material has flexibility which allows a deformation of the wall.

For the embodiment of the above-mentioned flexible wall type, in order to obtain an appropriate pumping effect and thus limit the number of pumping cycles necessary for the mixing of the beneficial agent with the liquid, the chamber should not be too full of the beneficial agent. Conveniently, at least 30% of the volume of the chamber is empty in the un-squeezed state. Preferably, the volume of beneficial agent constitutes from 5% to 70%, preferably from 30% to 50% of the volume of the chamber. The limits of the ratio filled and un-filled volume will depend on the solubility of the product.

The liquid nutritional feeding composition is of a conventional type. The liquid nutritional feeding composition may comprise from 0 to 25% protein, from 0 to 50% lipids, and from 0 to 60% carbohydrates. For example, it may comprise about 15% protein, about 35% lipids, and about 50% carbohydrates. The water content is preferably from 70 to 95% by weight.

The chamber may be delivered as a sealed unit comprising the beneficial agent. Alternatively, the chamber may be filled with the beneficial agent at the location where the treatment is to take place.

The connection between the container, the chamber, and the feeding means are preferably as follows: an inlet is provided with a hollow spike for piercing of a port of the container and creating a fluid path for the nutritional feeding composition. The feeding means comprises a hollow spike for piercing the outlet of the chamber and creating a fluid path for the nutritional feeding composition with the beneficial agent. The piercing of the outlet of the chamber is done after end mixing. The present system of connection allows for on-line feeding of an aseptic liquid nutritional feeding composition with a beneficial agent.

The flow from the container to and through the feeding tube means may be due to gravity alone, but preferably the flow from the container to and through the feeding tube means is assisted by a pump.

The beneficial agent is dispersible in the nutritional liquid feed. By dispersible is understood, soluble as well as agents that are suspendable so as to be mixed with the liquid feed and forwarded herewith.

The beneficial agent or agents is/are, for e.g., selected from the group consisting of nutrients, probiotics, medicaments and diagnostic tracer or a physiological combination thereof.

It is preferred that the beneficial agent(s) is/are dispersible in the nutritional feeding composition in less than 1 min, more preferably in less than 30 sec.

For beneficial agents that are stable in liquid conditions, the agents may be provided in liquid form. Even if the beneficial agent is stable in a certain liquid formulation, a mixture of the liquid nutritional feeding composition and the liquid beneficial agent may not be stable for a longer period, thus the apparatus according to the invention may advantageously be used.

For enteral feeding the beneficial agents are cleaned but there is no need for a sterile product. However, for intravenously fed liquid, the beneficial agent must be sterilised.

The beneficial agent preferably comprises nutrients selected from the group consisting of glutamine, vitamins, arginine, fermentable and non-fermentable dietary fibres, enzymes, oligo elements, combinations of amino acids, oligosaccharides, short chain fatty acids, salts, structured lipids, d-cyroinositol, lactoferrin, marine oils, acidulents, antioxidants, or a combination thereof.

The apparatus according to the invention may advantageously be used for enteral or intravenous feeding. For intravenous feeding the beneficial agent is sterilised.

In a second aspect, the invention relates to a method for modifying and feeding a liquid nutritional feeding composition comprising, connecting a chamber, of the kind described above, to a container comprising a liquid nutritional feeding composition, pumping liquid feeding composition into the chamber, and liquid nutritional feeding composition and the beneficial agent back to the container to mix with the nutritional feeding composition, connecting the feeding means, and allowing the modified nutritional feeding composition to flow through the chamber into the feeding means.

BRIEF DESCRIPTION OF THE DRAWINGS

The present invention will now be described in further detail by way of examples only with reference to the accompanying drawings and examples, in which.

DETAILED DESCRIPTION OF THE PREFERRED EMBODIMENTS

Figure 1:
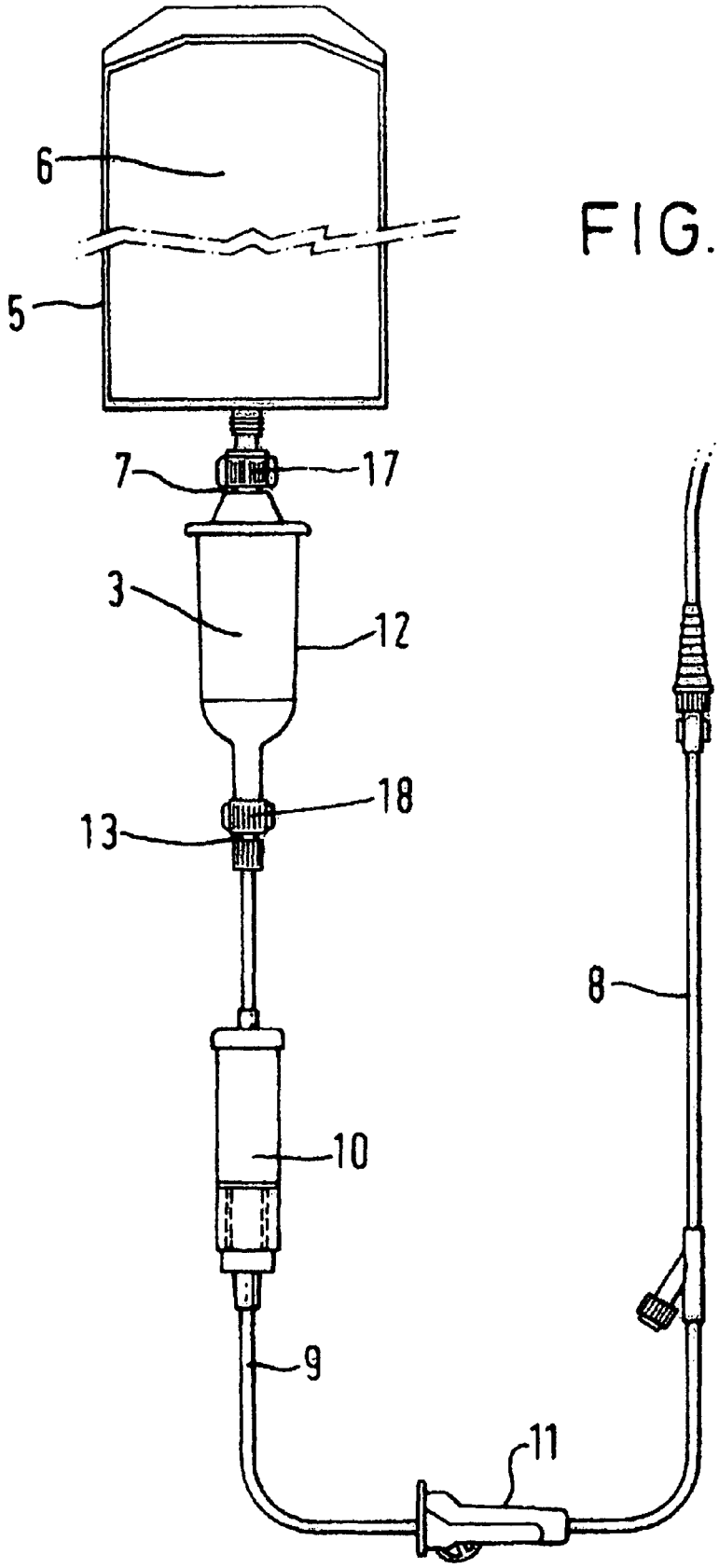
FIG. 1 is a principle drawing illustrating enteral feeding of a patient with an apparatus according to the invention.

FIG. 1 shows an apparatus 1 according to the invention arranged for modifying and feeding a liquid nutritional feed 6 to a patient, not shown in the drawings. The apparatus 1 comprises a chamber 3 containing a beneficial agent. The chamber 3 is connected to a container 5 containing the nutritional feeding composition 6 via an inlet 7. An outlet 13 in the chamber 3 is connected to feeding tubes 8 and 9 which serve to lead the modified feeding composition to the patient. The feeding tube 9 extends through the nasal path and to the stomach of the patient. Pumping means is provided in the form of the chamber 3 which has a flexible wall structure 12 for pumping the liquid feeding composition 6 into the chamber 3 and back to the container 5 so as to modify the liquid feeding composition 6. In order to assure attachment between the parts 5, 7, 8, 9 and 13, conventional fastening means 17 and 18 are provided. Furthermore, a pump 10 to assist the flow from the outlet 13 and flow regulation means 11 are provided.

Figure 2:
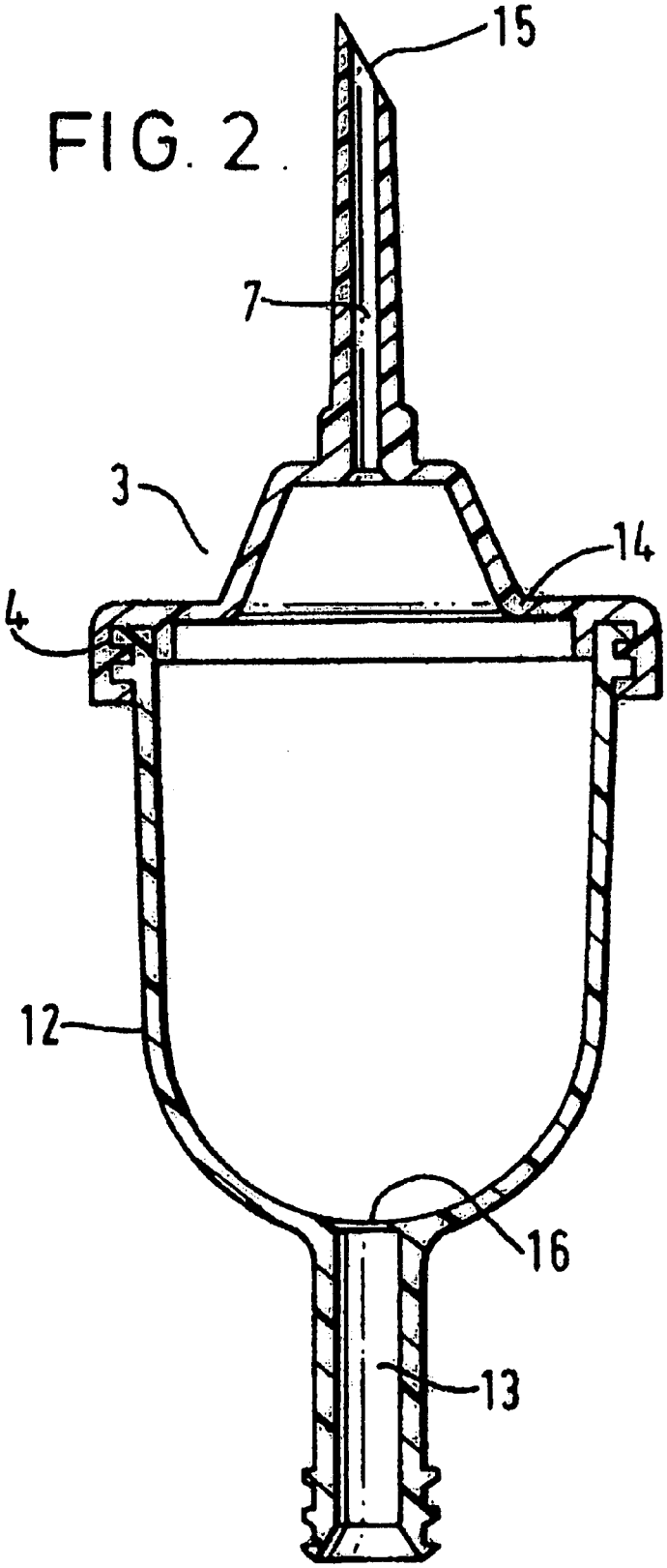
FIG. 2 is a cross-sectional principle drawing of the chamber for receiving a beneficial agent.

FIG. 2 illustrates a chamber 3 according to the invention. The chamber 3 comprises an inlet 7 and an outlet 13. A chamber wall 12 is provided in a flexible plastic, for e.g., soft Polyvinyl Chloride and a rigid lid 14 is made from a harder plastic, for e.g., hard Polyvinyl Chloride. In the present embodiment the inlet 7 is defined in the lid 14. The lid 14 may, for e.g., be sealed onto the wall 12 by ultrasonic welding or provided with threads 4 and screwed onto the wall 12.

Before use, the chamber 3 the inlet 7 and the outlet 13 are closed by thin membranes 15 and 16. For the initial mixing of a beneficial agent with a liquid feeding composition, the inlet's membrane 15 is first pierced when being connected to the container 5 shown in FIG. 1. Upon end pumping and mixing, the tube feeding 8 of FIG. 1 is to be connected to the chamber 3 which results in a piercing of the outlet's membrane 16.

EXAMPLE 1

Several liquid nutritional feeding compositions are modified and fed by 1) connecting containers of liquid, feeding to a flexible chamber according to the invention, by piercing the port in the container with the spike of the container,
2) pumping liquid from the container to the chamber and back agent by squeezing and releasing the chamber 3 to 5 times, and
3) connecting the feeding means by piercing the outlet of the chamber, thus feeding the modified liquid feed composition to the feeding means. The flow is by gravity or assisted by a pump.

Test are, for example, carried out by feeding.

1) 12 g glutamine as beneficial agent constituting about 60% of the volume of the chamber with 500 ml or 1 L liquid feed.
2) 1 g pro-biotic as beneficial agent constituting about 5% of the volume of the chamber with 500 ml of 1 L liquid feed.
3) 12 g glutamine mixed with 1 g pro-biotic as beneficial agent constituting in total about 65% of the volume of the chamber with 500 ml of 1 L liquid feed.

The liquid feeds are commercially available products such as Réabilan HN, Réabilan, Sondalis ISO, and Sondalis HP supplied by Nestlé S.A. Switzerland.

The modified feed is inspected and characterised as homogeneous.

EXAMPLE 2

Stability

The stability of the mixture of the liquid nutritional feeding composition and the beneficial agent are controlled by the level of beneficial agent as measured by means of a calorimetric method (Kit Boehringer).

Mixtures of liquid nutritional feeding composition and beneficial agent are fed and samples are stored for 24 hours and 48 hours and the level of beneficial agent is measured.

For example, the stability of Sondalis SO and Réabilan HN comprising Glutamine are measured over this period:

| | Sondalis ISO | Réabilan HN |
|---|---|---|
| T = 0 h | 12.9 g/l | 14.6 g/l |
| T = 24 h | 12.6 g/l | 13.5 g/l |
| T = 48 h | 12.5 g/l | 12.9 g/l |

The measurements show that the Glutamine is stable above a level of 12 g/l after 48 hours.

EXAMPLE 3

Homogenisation

The homogeneity of the modified liquid nutritional feeding composition is controlled by mixing the beneficial agent or agents with the liquid nutritional feeding composition by pumping 5 times the liquid into and out of the chamber.

The feeding tube or line is connected to the chamber and an enteral pump running at 100 ml/h, corresponding to a continuous nutrition (24 h/42 h).

During the feeding, after each 50 ml fed, the level of beneficial agent is measured by means of a calorimetric method (Kit Boehringer).

Figure 3:
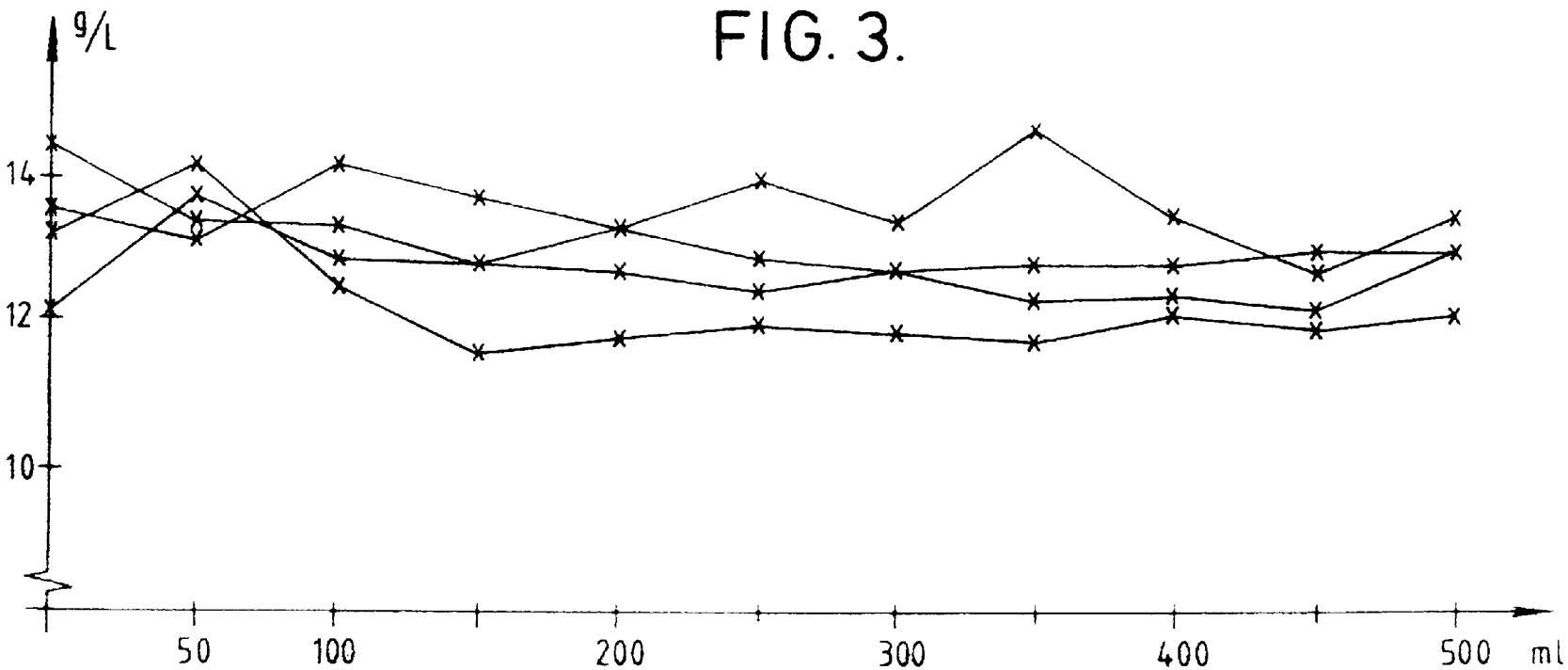
FIG. 3 shows a measure of levels of beneficial agent in a feed.

FIG. 3 shows the amount of beneficial agent in a feed, in the example in question the beneficial agent is Glutamine in 500 ml of 4 different liquid feeding compositions. It is apparent from the figure that the Glutamine level is homogeneous at about 12–14 g/l during the feeding period.

EXAMPLE 4

In order to verify that the geometry of the liquid containing container did not influence the homogenisation of the modified feed, trials were conducted with drip-pack, plastic pouches, and glass bottles. No difference in the homogeneity was detected from the various containers.

What is claimed is:

1. An apparatus for modifying and feeding, a liquid nutritional feeding composition comprising:

a chamber comprising a beneficial agent for modifying a liquid nutritional feeding composition, the chamber having an inlet connectable to a container containing the nutritional feeding composition and an outlet connectable to a feeding means, and a pumping means associated with the chamber wherein said pumping means is adapted for pumping said nutritional feeding composition from the container into the chamber and back to the container for mixing the beneficial agent into the nutritional feeding composition.

2. An apparatus according to claim 1, wherein the pumping means comprises means for varying the volume of the chamber.

3. An apparatus according to claim 2, wherein the chamber comprises at least one flexible wall capable of being squeezed and released for pumping of the nutritional feeding composition.

4. An apparatus according to claim 1, wherein the chamber comprises at least one beneficial agent selected from the group consisting of nutrients, probiotics, medicaments, diagnostic agents and mixtures thereof.

5. An apparatus according to claim 1, wherein the at least one beneficial agent is dispersible in the nutritional feeding composition in less than 1 min.

6. An apparatus according to claim 1, wherein the at least one beneficial agent is dispersible in the nutritional feeding composition in less than 30 sec.

7. An apparatus according to claim 4, wherein the volume of beneficial agent contributes from: 30% to 50% of the volume of the chamber.

8. An apparatus according to claim 1, wherein the inlet is provided with a hollow spike for piercing a port on the container to create a fluid path for the nutritional feeding composition.

9. An apparatus according to claim 1, wherein the feeding means comprises a hollow spike for piercing the outlet of the chamber to create a fluid path for the nutritional feeding composition with the beneficial agent.

10. A method for modifying and feeding a liquid nutritional feeding composition comprising:

connecting a chamber according to claim 1 to a container comprising a liquid nutritional feeding composition, pumping liquid feeding composition into the chamber and liquid nutritional feeding composition and beneficial agent back to the container to mix the nutritional feeding composition with the beneficial agent, connecting the feeding means to the outlet of the chamber, and allowing the modified nutritional feeding composition to flow through the chamber into the feeding means.

11. The method of claim 10 wherein the feeding involves enterally supplying the liquid nutritional feeding composition.

12. The method of claim 10 wherein the feeding involves intravenously supplying the liquid nutritional feeding composition.

13. An apparatus according to claim 1, wherein the volume of beneficial agent constitutes from [30] *5%* to [50] *70%* of the volume of the chamber.

14. An apparatus according to claim 1, wherein the nutritional composition contains protein in an amount of up to 25%, lipids in an amount of up to 50%, and carbohydrates in an amount of up to 60%.

*15. An apparatus for modifying and feeding a liquid nutritional feeding composition comprising:*

*a container containing the nutritional feeding composition comprising protein in an amount of up to 25%, lipids in an amount of up to 50%, and carbohydrates in an amount of up to 60%;*

*a chamber comprising a beneficial agent for modifying a liquid nutritional feeding composition, the chamber having an inlet connectable to the container containing the nutritional feeding composition and an outlet connectable to a feeding means, and*

*a pumping means associated with the chamber wherein said pumping means is adapted for pumping said nutritional feeding composition from the container into the chamber and back to the container for mixing the beneficial agent into the nutritional feeding composition;*

*wherein the at least one beneficial agent is selected from the group consisting of nutrients, probiotics, medicaments, diagnostic agents and mixtures thereof, and constitutes from 30% to 50% of the volume of the chamber, and further wherein the at least one beneficial agent is dispersible in the nutritional feeding composition in less than 1 min.*

*16. The apparatus of claim 15, wherein the volume of beneficial agent constitutes from 5% to 70% of the volume of the chamber and further wherein the at least one beneficial agent is dispersible in the nutritional feeding composition in less than 30 sec.*

* * * * *

UNITED STATES PATENT AND TRADEMARK OFFICE

CERTIFICATE OF CORRECTION

PATENT NO. : RE 41,159 E
APPLICATION NO. : 10/194725
DATED : March 2, 2010
INVENTOR(S) : Bourguignon It is certified that error appears in the above-identified patent and that said Letters Patent is hereby corrected as shown below:

Title Page:
Item (73) Assignee, after "Nestec S.A., Vevey" change "(SE)" to -- (CH) --.

Column 5:
Line 39 (claim 1, line 1), after "An apparatus for modifying and feeding" delete ",".

Column 6:
Line 2 (claim 7, line 2), change "contributes from:" to -- constitutes from --.

Signed and Sealed this

Twentieth Day of April, 2010

David J. Kappos

David J. Kappos
*Director of the United States Patent and Trademark Office*